United States Patent
Albers et al.

(10) Patent No.: US 7,045,494 B2
(45) Date of Patent: May 16, 2006

(54) ALKYL AND/OR ALKENYLOLIGOGLYCOSIDE PREPARATIONS HAVING REDUCED MAGNESIUM SALT CONCENTRATIONS

(75) Inventors: Thomas Albers, Haltern (DE); Karl Heinz Schmid, Mettmann (DE); Rainer Eskuchen, Langenfeld (DE); Michael Koehler, Mettmann (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 10 days.

(21) Appl. No.: 10/481,841

(22) PCT Filed: Jun. 12, 2002

(86) PCT No.: PCT/EP02/06425

§ 371 (c)(1),
(2), (4) Date: Dec. 22, 2003

(87) PCT Pub. No.: WO03/000710

PCT Pub. Date: Jan. 3, 2003

(65) Prior Publication Data

US 2005/0176616 A1    Aug. 11, 2005

(30) Foreign Application Priority Data

Jun. 21, 2001   (DE) ................................ 101 29 484

(51) Int. Cl.
C11D 3/22 (2006.01)
C11D 11/00 (2006.01)
C11D 13/00 (2006.01)
C07H 15/04 (2006.01)

(52) U.S. Cl. .............. 510/470; 510/474; 510/535; 514/23; 514/54; 536/123.1; 536/124

(58) Field of Classification Search ............ 510/470, 510/474, 535; 514/23, 54; 536/123.1, 124
See application file for complete search history.

(56) References Cited

U.S. PATENT DOCUMENTS 6,100,391 A * 8/2000 Gibson et al. .............. 536/124

FOREIGN PATENT DOCUMENTS

WO    WO 99/26957    6/1999

OTHER PUBLICATIONS

Biermann et al., Alkylpolyglucoside—Technologie und Eigenschaften, Starch Starke, vol. 45, 1993, pp. 281-288, no month given.
Barry Salka, "Alkyl Polyglycosides", Cosmetics & Toiletries, vol. 108, 1993, pp. 89-94, Mar. 1993.
Kahre et al., Alkylpolyglycoside—Ein neues Konzept fuer Pflege und Vertraeglichkeit in der Kosmetei, SÖFW Journal, vol. 121, 1995, pp. 598, 600, 601, 604-611, Aug. 1995.

* cited by examiner

Primary Examiner—Brian P. Mruk
(74) Attorney, Agent, or Firm—John F. Daniels; Arthur G. Seifert

(57) ABSTRACT

A process for making an alkyl and/or alkenyl oligoglycoside preparation having a magnesium salt concentration of less than about 10 ppm involving the steps of: (a) providing an alkyl and/or alkenyl oligoglycoside preparation having an active substance content of from about 10 to 70% by weight, based on the weight of the preparation; (b) providing an acid component; (c) adjusting the pH of the alkyl and/or alkenyl oligoglycoside preparation to from about 4 to 9.5 by combining the acid component with the alkyl and/or alkenyl oligoglycoside preparation to form a pH-modified alkyl and/or alkenyl oligoglycoside preparation; (d) providing a column charged with an ion exchange resin; and (e) purifying the pH-modified alkyl and/or alkenyl oligoglycoside preparation by passing it through the column of step (d) at a viscosity of from about 20 to 6,000 mPas, and at a temperature of from about 20 to 90° C. to form the alkyl and/or alkenyl oligoglycoside preparation having a magnesium salt concentration of less than about 10 ppm.

10 Claims, No Drawings

ALKYL AND/OR ALKENYLOLIGOGLYCOSIDE PREPARATIONS HAVING REDUCED MAGNESIUM SALT CONCENTRATIONS

This application is a 371 of PCT/EP02/06425 filed Jun. 12, 2002.

BACKGROUND OF THE INVENTION

This invention relates to alkyl and/or alkenyl oligoglycoside preparations with a magnesium salt concentration of less than 10 ppm which are obtained by adjusting alkyl and/or alkenyl oligoglycoside preparations to a certain pH range and then purifying them in a column charged with an ion exchange resin and to a process for the production of these preparations.

In the production of alkyl and/or alkenyl oligoglycosides by reaction of fatty alcohols with glucose, magnesium oxide is added during the synthesis. In order to ensure that alkyl and/or alkenyl oligoglycosides have high stabilities in storage without the addition of preservatives, preparations of the type in question have to be adjusted to basic pH values. At pH values above 11.3 in particular, unwanted clouding occurs or a deposit attributable to precipitation of the magnesium oxide is formed. Although treatment of the alkyl and/or alkenyl oligoglycoside preparations with complexing agents does lead to clear pastes in the interim, the magnesium salts still present in the solution may possibly be released as poorly soluble salts during subsequent processing.

Accordingly, the problem addressed by the present invention was to provide alkyl and/or alkenyl oligoglycoside preparations which would contain reduced concentrations of magnesium salts, which would also be color-stable at basic pH values and which would optionally show microbial stability and would therefore not produce any clouding over the entire pH range. In addition, the invention set out to provide a simple and inexpensive process for the production of these preparations.

DESCRIPTION OF THE INVENTION

The present invention relates to alkyl and/or alkenyl oligoglycoside preparations with a magnesium salt concentration below 10 ppm, based on the composition as a whole, obtainable by adjusting alkyl and/or alkenyl oligoglycoside preparations with an active substance content of 10 to 70, preferably 20 to 67 and more particularly 40 to 65% by weight, based on the composition as a whole, with acids to a pH of 4 to 9.5, preferably 5 to 9 and more particularly 6 to 8 and then purifying the preparations in a column charged with an ion exchange resin, with the proviso that the alkyl and/or alkenyl oligoglycoside preparations are applied to the column with a viscosity of 20 to 6,000, preferably 50 to 600 and more particularly 100 to 400 mPas (Brookfield, RVF viscosimeter, spindle 5, 10 r.p.m.) and at a temperature of 20 to 90, preferably 30 to 80 and more particularly 40 to 70° C.

The present invention also relates to a process for removing magnesium salts from alkyl and/or alkenyl oligoglycosides in which alkyl and/or alkenyl oligoglycoside preparations with an active substance content of 10 to 70% by weight, based on the composition as a whole, are adjusted with acids to a pH of 4 to 9.5, preferably 5 to 9 and more particularly 6 to 8 and are then purified in a column charged with an ion exchange resin, with the proviso that the alkyl and/or alkenyl oligoglycoside preparations are applied to the column with a viscosity of 20 to 6,000, preferably 50 to 600 and more particularly 100 to 400 mPas (Brookfield, RVF viscosimeter, spindle 5, 10 r.p.m.) and at a temperature of 20 to 90, preferably 30 to 80 and more particularly 40 to 70° C.

It has surprisingly been found that alkyl and/or alkenyl oligoglycoside preparations with a reduced magnesium salt concentration (<10 ppm) can be obtained by first adjusting alkyl and/or alkenyl oligoglycoside preparations having a certain viscosity and concentration with acids to a certain pH value and then purifying the preparations in a column charged with an ion exchange resin. A particular advantage is that the purified preparations are also color-stable at basic pH values and even show microbial stability at pH values above 11.5. Accordingly, such preparations do not produce any unwanted clouding over the entire pH range. The alkyl and/or alkenyl oligoglycoside preparations with reduced magnesium salt concentrations are comparatively simple and relatively inexpensive to produce.

Alkyl and/or Alkenyl Oligoglycosides

The alkyl and alkenyl oligoglycosides according to the invention correspond to formula (I):

$$R^1O\text{-}[G]_p \qquad (I)$$

where $R^1$ is an alkyl and/or alkenyl group containing 4 to 22 carbon atoms and preferably 8 to 18 carbon atoms, G is a sugar unit containing 5 or 6 and preferably 6 carbon atoms and p is a number of 1 to 10. They may be obtained by the relevant methods of preparative organic chemistry. The overviews presented by Bierman et al. in Starch/Stärke 45, 281 (1993), by B. Salka in Cosm. Toil. 108, 89 (1993) and by J. Kahre in SÖFW-Journal No. 8, 598 (1995) are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational perspective. The alkyl or alkenyl group $R^1$ may be derived from primary alcohols containing 4 to 2 and preferably 8 to 11 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl group $R^1$ may also be derived from primary alcohols containing 12 to 18 and more particularly 12 to 14 and 16 to 18 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Alkyl and/or alkenyl oligoglycoside preparations with a magnesium concentration of 50 to 2,500, preferably 100 to 1,000 and more particularly 400 to 600 ppm, based on the composition as a whole, are preferably purified. Magnesium salts in the context of the invention are understood to be magnesium/magnesium hydroxide, magnesium carbonates, magnesium halides and preferably magnesium oxide. Alkyl and/or alkenyl oligoglycoside preparations with an active substance content of 10 to 70, preferably 20 to 67 and more particularly 40 to 65% by weight are preferably used for the purposes of the invention.

Ion Exchange Resins (Resins)

Ion exchangers are solids or liquid solutions which are capable of taking up positively or negatively charged ions from an aqueous electrolyte solution and releasing equivalent quantities of other ions. Ion exchangers are known as cation or anion exchangers according to the electrical charge of the ions involved in the exchange. In addition, the ion exchangers may be classified according to their matrix and functional groups. Solid granules and particles of ion exchange resins of which the matrix has been obtained by condensation (phenol-formaldehyde) or by polymerization (copolymers of styrene and divinyl benzene and methacrylates and divinyl benzene) are the most commonly used.

Ion exchange resins of which the matrix consists of styrene/divinyl benzene copolymers and which contain chelating groups carrying O, N, S or P atoms as functional groups and which are therefore suitable for the exchange of magnesium salt ions are used in accordance with the present invention. The chelating groups include, for example, sulfonic acid, carboxyl, aminomethyl phosphonic acid and iminodiacetate groups. Preferred functional groups are aminomethylphosphonic acid, iminodiacetate and sulfonic acid groups such as, for example, Lewatit TP 260 (with aminomethyl phosphonic acid groups) and Lewatit TP 207 and Lewatit 208 (with iminodiacetate groups) from Bayer AG or Dowex Marathon C, Dowex Marathon C-10, Dowex Monosphere C 400, Dowex Marathon MSC (with sulfonic acid groups) from Dow or Amberlite 200 C, Amberlite 252, Amberlite IR120 (with sulfonic acid groups) from Rohm & Haas. Lewatit TP 260 is particularly preferred and Lewatit TP 207 and Lewatit TP 208 most particularly preferred.

PROCESS

Regeneration and Conditioning of the Exchange Resin

The purification of the alkyl and/or alkenyl oligoglycoside preparations is carried out with a regenerated and subsequently conditioned ion exchange resin. To this end, an ion exchange column is filled with the ion exchange resin (resin), regenerated with 2 filling volumes of 2-molar hydrochloric acid and then washed with 4 filling volumes of water. The resin is conditioned with 1 to 2 filling volumes of 1-molar sodium hydroxide, preferably with 2 filling volumes, and is then washed with 3 to 4 filling volumes of water. Where Lewatit TP 207, for example, is used, conditioning leads to the mono- and/or disodium form of the iminodiacetate exchange resin and preferably to the disodium form. The flow rate during regeneration and conditioning is preferably 1 to 2 mm per second. With a capacity of ca. 1 kg resin, up to ca. 100 kg alkyl and/or alkenyl oligoglycoside preparation can be purified.

Treatment of the Alkyl and/or Alkenyl Oligoglycoside Preparations

The alkyl and/or alkenyl oligoglycoside preparations are preheated to a temperature of 20 to 90° C., preferably to a temperature of 30 to 80° C. and more particularly to a temperature of 40 to 70° C. and adjusted with an acid to a pH of 3 to 9.5, preferably to a pH of 4 to 9 and more particularly to a pH of 6 to 8. The pH of the alkyl and/or alkenyl oligoglycoside preparations is preferably adjusted with mineral acids or organic acids. In one particular embodiment of the invention, the pH is adjusted with a 50% mineral acid such as, for example, sulfuric acid, hydrochloric acid or a 50% organic acid, for example citric acid or tartaric acid.

The viscosity of the treated alkyl and/or alkenyl oligoglycoside preparation should be between 20 and 6,000, preferably between 50 and 600 and more particularly between 100 and 400 mPas.

If the magnesium salts are removed from the alkyl and/or alkenyl oligoglycoside preparations by passage through an ion exchange column and not by addition of the exchanger to the preparation (with stirring and a prolonged residence time), followed by removal of the ion exchanger by filtration after removal of the salts, the treated preparation should have a viscosity of 20 to 6,000 mPas, preferably 50 to 600 mPas and more particularly 100 to 400 mPas (Brookfield, spindle 5, 10 r.p.m.). It is possible in this way to avoid an excessive pressure loss in the ion exchange column and to guarantee a flow rate of up to 10 mm per second—optionally by applying a slight excess pressure of 0.1 to 2 bar, in which case the column is externally heated to the temperature of the preheated alkyl and/or alkenyl oligoglycoside preparation. If the alkyl and/or alkenyl oligoglycoside preparations have relatively high viscosities, they are heated to temperatures of 20 to 90° C., preferably to temperatures of 30 to 80° C. and more particularly to temperatures of 40 to 70° C. in order to reduce their viscosity.

The preparation is applied with the above-mentioned viscosity to the ion exchange column containing the regenerated and conditioned exchange resin (resin) and the effluent from the column is tested for its magnesium content. Alkyl and/or alkenyl oligoglycoside preparations with a concentration of <10, preferably <7 and more particularly <1 ppm magnesium salts, based on the composition as a whole, can be obtained by this process.

In one particular embodiment of the invention, the treated alkyl and/or alkenyl oligoglycoside preparation is pump-circulated through the ion exchange column until its magnesium content is <10, preferably <7 and more particularly <1 ppm. Testing of the magnesium content is carried out by any of the standard analytical methods (for example by ICP chromatography [Q-C 2085.0] or by a photometric assay—Dr. Lange cuvette test, LCK 326).

In another process variant, the ion exchange resin can also be introduced into the neutralized alkyl and/or alkenyl oligoglycoside preparation which is then stirred until the magnesium content has fallen below the required magnesium content and subsequently filtered trough a 400 µm bag filter to remove the ion exchange resin.

The purified alkyl and/or alkenyl oligoglycoside preparations may then be adjusted to a basic pH, for example by treatment with an anion exchanger. This neutralization step removes the anions introduced during neutralization from the preparation and, on the other hand, re-establishes the original basic pH, for example above 11.3.

Accordingly, in a preferred embodiment of the invention, alkyl and/or alkenyl oligoglycoside preparations with a magnesium salt concentration <10, preferably <7 and more particularly <1 ppm, based on the composition as a whole, are obtained by adjusting alkyl and/or alkenyl oligoglycoside preparations with an active substance content of 20 to 67 and more particularly 40 to 65% by weight to a pH of 4 to 9 and more particularly 6 to 8 with mineral acids or organic acids at temperatures of 30 to 80° C. and more particularly 40 to 70° C. and then purifying the preparations at a viscosity of 50 to 600 and preferably 100 to 400 mPas (Brookfield, RVF viscosimeter, spindle 5, 10 r.p.m.) in an ion exchange column charged with a regenerated and subsequently conditioned ion exchange resin.

COMMERCIAL APPLICATIONS

The alkyl and/or alkenyl oligoglycoside preparations according to the invention with magnesium salt concentrations <10 ppm may be used in any of the surface-active preparations known to the expert and are preferably used in laundry and dishwashing detergents, household cleaners and cosmetic and/or pharmaceutical preparations and more particularly in cosmetic hair care and body care preparations and also in cleaners, such as glass cleaners for example. These surface-active preparations may contain pearlizing waxes, consistency factors, thickeners, superfatting agents, stabilizers, silicone compounds, fats, waxes, lecithins, phospholipids, antioxidants, deodorants, antiperspirants, antidandruff components, swelling agents, tyrosine inhibitors, hydrotropes, solubilizers, preservatives, perfume oils, dyes, other surfactants and the like as further auxiliaries and additives. The cosmetic and/or pharmaceutical preparations include, for example, oral hygiene and dental care preparations, hair shampoos, hair lotions, foam baths, shower baths, creams, gels, lotions, alcoholic and hydroalcoholic solutions and emulsions.

EXAMPLES

1. Regeneration and Conditioning of the Exchange Resin

An ion exchange column with a volume of 10 liters was filled with 2 kg Lewatit TP 207 (Bayer), regenerated with 5.4 liters 2-molar hydrochloric acid and then washed with 10.8 liters water. Conditioning was carried out with 2.7 liters 1-molar sodium hydroxide and was followed by washing with 10.8 liters water. The flow rate during regeneration and conditioning was 1.4 mm per second.

2. Treatment of Glucopon 215 CSUP ($C_{8/10}$ Alkyl and/or Alkenyl Oligoglycoside)

50 kg Glucopon 215 CSUP (63 to 65% by weight active substance content) with a magnesium salt content of 750 ppm were preheated to 70° C. and adjusted to a pH of ca. 6.7 with a 30% sulfuric acid (ca. 1,600 ml). This preparation flowed through the ion exchange column at a flow rate of up to 10 mm per second, optionally by application of a slight excess pressure of 0.1 to 1 bar at a temperature of 70° C. through external heating of the column. The magnesium content of the treated Glucopon 215 CSUP was monitored in the effluent of the ion exchange column by ICP (atomic fluorescence spectroscopy). The concentration of magnesium salts in the preparation was below 10 ppm.

3. Storage Tests

Glucopon 215 CSUP (63 to 65% by weight active substance content) with a magnesium salt content of 750 ppm and a pH of 11.5 was stored for 4 weeks at 60° C. in 1 1-liter glass bottle. At the end of this period, a deposit of magnesium hydroxide of ca. 10% of the total volume had accumulated in the glass bottle.

The Glucopon 215 CSUP purified in accordance with Example 2 was adjusted to a pH of 11.5 with 50% sodium hydroxide and stored for 4 weeks at 60° C. in a 1-liter glass bottle. At the end of this period, the product was deposit-free and as clear as at the beginning of the storage test.

The invention claimed is:

1. A process for making an alkyl and/or alkenyl oligoglycoside preparation having a magnesium salt concentration of less than about 10 ppm comprising:
    (a) providing an alkyl and/or alkenyl oligoglycoside preparation having an active substance content of from about 10 to 70% by weight, based on the weight of the preparation, and having more than 10 ppm of magnesium;
    (b) providing an acid component;
    (c) adjusting the pH of the alkyl and/or alkenyl oligoglycoside preparation to from about 4 to 9.5 by combining the acid component with the alkyl and/or alkenyl oligoglycoside preparation to form a pH-modified alkyl and/or alkenyl oligoglycoside preparation;
    (d) providing a column charged with an ion exchange resin; and
    (e) purifying the pH-modified alkyl and/or alkenyl oligoglycoside preparation by passing it through the column of step (d) at a viscosity of from about 20 to 6,000 mPas, and at a temperature of from about 20 to 90° C. to form the alkyl and/or alkenyl oligoglycoside preparation having a magnesium salt concentration of less than about 10 ppm.

2. The process of claim 1 wherein the preparation of step (a) has an active substance content of from about 20 to 67% by weight, based on the weight of the preparation.

3. The process of claim 1 wherein the preparation of step (a) has an active substance content of from about 40 to 65% by weight, based on the weight of the preparation.

4. The process of claim 1 wherein the pH of the preparation of step (a) is adjusted to from about 5 to 9.

5. The process of claim 1 wherein the pH of the preparation of step (a) is adjusted to from about 6 to 8.

6. The process of claim 1 wherein the pH-modified alkyl and/or alkenyl oligoglycoside preparation of step (e) has a viscosity, prior to entering the column, of from about 50 to 600 mPas.

7. The process of claim 1 wherein the pH-modified alkyl and/or alkenyl oligoglycoside preparation of step (e) has a viscosity, prior to entering the column, of from about 100 to 400 mPas.

8. The process of claim 1 wherein the alkyl and/or alkenyl oligoglycoside preparation is passed through the column at a temperature of from about 30 to 80° C.

9. The process of claim 1 wherein the alkyl and/or alkenyl oligoglycoside preparation is passed through the column at a temperature of from about 40 to 70° C.

10. The process of claim 1 wherein the acid component is selected from the group consisting of a mineral acid, an organic acid, and mixtures thereof.

* * * * *